US010220418B2

(12) United States Patent
Bitton

(10) Patent No.: US 10,220,418 B2
(45) Date of Patent: Mar. 5, 2019

(54) METHOD AND SYSTEM FOR RECYCLING ALUMINUM ALLOY RIMS USING SPECTROGRAPHIC ANALYSIS

(71) Applicant: Daniel Bitton, Toronto (CA)

(72) Inventor: Daniel Bitton, Toronto (CA)

(73) Assignee: House of Metals Company Limited, Toronto (CA)

( * ) Notice: Subject to any disclaimer, the term of this patent is extended or adjusted under 35 U.S.C. 154(b) by 162 days.

(21) Appl. No.: 15/333,361

(22) Filed: Oct. 25, 2016

(65) Prior Publication Data

US 2017/0173636 A1    Jun. 22, 2017

Related U.S. Application Data

(60) Provisional application No. 62/271,059, filed on Dec. 22, 2015.

(51) Int. Cl.
*B07C 5/34* (2006.01)
*G01N 21/71* (2006.01)
*G01G 19/414* (2006.01)

(52) U.S. Cl.
CPC ............. *B07C 5/34* (2013.01); *G01N 21/718* (2013.01)

(58) Field of Classification Search
CPC .................................. B07C 5/34; G01N 21/718
See application file for complete search history.

(56) References Cited

U.S. PATENT DOCUMENTS 8,322,639 B2 * 12/2012 Gitschel ................. B02C 23/08
                                                        241/19
9,475,652 B2 * 10/2016 Nichols ................. B07C 5/3422

* cited by examiner

*Primary Examiner* — John C Hong
(74) *Attorney, Agent, or Firm* — Bereskin & Parr LLP/S.E.N.C.R.L., s.r.l.

(57) ABSTRACT

A method and system of recycling aluminum alloy rims, the method and system comprising providing a feed of a plurality of aluminum alloy rims of different alloys, for each rim in the feed of aluminum alloy rims, determining a composition of that aluminum alloy rim, determining a plurality of recycled aluminum alloy composition ranges, and dividing the feed of aluminum alloy rims into a plurality of batches of aluminum alloy rims, each batch of aluminum alloy rims in the plurality of batches of aluminum alloy rims corresponding to an associated recycled aluminum alloy composition range in the plurality of recycled aluminum composition ranges, such that each rim in the plurality of aluminum alloy rims is allocated to an associated batch in the plurality of batches of aluminum alloy rims based on the composition of that aluminum alloy rim.

14 Claims, 3 Drawing Sheets

My method and system for recycling
aluminum alloy rims using
spectrographic analysis

RELATED APPLICATIONS

This application claims priority from the U.S. Patent Application No. 62/271,059, filed Dec. 22, 2015 entitled "METHOD AND SYSTEM FOR RECYCLING ALUMINUM ALLOY RIMS USING SPECTROGRAPHIC ANALYSIS", which is incorporated herein, in its entirety, by reference.

TECHNICAL FIELD

The embodiments disclosed herein relate to recycling processes and in particular to methods and systems for recycling aluminium alloy rims.

INTRODUCTION

Aluminum has a relatively low density and high strength. Accordingly, aluminum by itself or alloyed with other metals is useful in many applications as it permits light weight constructions. For example, aluminum car rims can be made of high purity aluminum alloy, including from Aluminum Association alloy number A356.2, as well as other alloys. Car rims may be anodized, coated with paint, clearcoat, chrome and/or other metal plating, and may contain components such as: lead weights, brass, rubber, brass fittings, stainless steel and iron inserts. If, for example, a rim made from Aluminum Association alloy number A356.2 is melted without removing these materials and components, then the composition of the melt may vary from the specification of alloy A356.2 and the melt may not be suitable for use in casting new alloy wheels made from alloy A356.2. As a result, aluminum alloy wheels rims are often recycled to produce less valuable products.

SUMMARY

A method of recycling aluminum alloy rims is disclosed. In one implementation, the method may comprise providing a feed of a plurality of aluminum alloy rims from vehicles, and for each rim in the feed of aluminum alloy rims, determining a composition of that aluminum alloy rim, determining a plurality of recycled aluminum alloy composition ranges, and dividing the feed of aluminum alloy rims into a plurality of batches of aluminum alloy rims, each batch of aluminum alloy rims in the plurality of batches of aluminum alloy rims corresponding to an associated recycled aluminum alloy composition range in the plurality of recycled aluminum composition ranges. Each rim in the plurality of aluminum alloy rims may be assigned or allocated to an associated batch in the plurality of batches of aluminum alloy rims based on the composition of that aluminum alloy rim.

In other implementations, the method may comprise, for each batch of aluminum alloy rims in the plurality of aluminum alloy rims, determining, updating and storing batch-specific variables, wherein the batch-specific variables comprise a batch-specific total weight of aluminum alloy rims previously allocated to that batch, and a batch-specific average composition of aluminum alloy rims previously allocated to that batch. The batch-specific average composition of aluminum alloy rims previously allocated to that batch may be calculated based on the weight and the composition of each aluminum alloy rim previously allocated to that batch. For each aluminum alloy rim, the method may include allocating that aluminum alloy rim to the associated batch in the plurality of batches of aluminum alloy rims is based on, in addition to the composition of that aluminum alloy rim and the weight of that aluminum alloy rim, the batch-specific total weight of aluminum alloy rims previously allocated to that batch and the batch-specific average composition of aluminum alloy rims previously allocated to that batch.

According to a further aspect, the determining the composition of each aluminum alloy rim may be performed using a composition analyzer. Determining the composition may include exposing a portion of a bare metal surface of each aluminum alloy rim before determining the composition of that aluminum alloy rim, and determining a composition of the material from which the rim is made at that portion of the bare metal surface.

A system for recycling aluminum alloy rims is also disclosed. The system may comprise an aluminum alloy rim transfer mechanism for providing a feed of a plurality of aluminum alloy rims of different alloys to a composition analyzer, for example a laser spectroscopy analyzer, for determining a composition of each rim. That is, the composition analyzer may be operable to determine the composition of each rim in the plurality of aluminum alloy rims. The transfer mechanism may include any suitable (for the geometry and size of the rims to be recycled) one or more of, or a combination of one or more of: a conveyor, a pick-and-place unit, a robotic arm, and other relevant technologies known in the art. The composition analyzer may be positioned to receive each rim in the plurality of aluminum alloy rims from the aluminum alloy rim transfer mechanism.

Similar transfer mechanisms may be employed to transport the rims from the composition analyzer to other stations in the recycling process, and between the other stations (as will be described below) that may be part of the recycling process. The system may also include a computer comprising a non-transient memory and a processor in electronic communication with the non-transient memory, the non-transient memory having stored thereon a plurality of recycled aluminum alloy composition ranges, the computer being in electronic communication with the composition analyzer to receive, for each rim in the plurality of aluminum alloy rims, the composition of that rim, and the processor being operable to allocate each rim to a batch in a plurality of batches of aluminum alloy rims based on the composition of that rim. According to other embodiments, the system may include a weigh scale for determining a weight of each rim and may also include storing batch-specific variables and carrying out one or more of the implementations of the method of recycling aluminum alloy rims described above.

Other implementations and embodiments of the method and system for recycling aluminum alloy rims will be described in the detailed description section below. Other aspects and features will become apparent, to those ordinarily skilled in the art, upon review of the following description of some exemplary implementations and embodiments.

BRIEF DESCRIPTION OF THE DRAWINGS

The drawings included herewith are for illustrating various examples of articles, methods, and apparatuses of the present specification. In the drawings.

DETAILED DESCRIPTION

Various embodiments of a method of recycling aluminum alloy rims and various embodiments of a system for recycling aluminum alloy rims will be described below to provide examples of each claimed invention. No embodiment described below limits any claimed invention and any claimed invention may cover methods or systems that differ from those described below. The claimed inventions are not limited to methods or systems having all of the features of any embodiment described below. It is possible that a method, apparatus, process, or system described below is not an embodiment of any claimed invention. Any invention disclosed below that is not claimed in this document may be the subject matter of another protective instrument, for example, a continuing patent application, and the applicants, inventors or owners do not intend to abandon, disclaim or dedicate to the public any such invention by its disclosure in this document.

Numerous specific details are set forth below in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not considered as limiting the scope of the embodiments described herein in any way, but rather as merely describing the implementation of the embodiments described herein.

Figure 1:
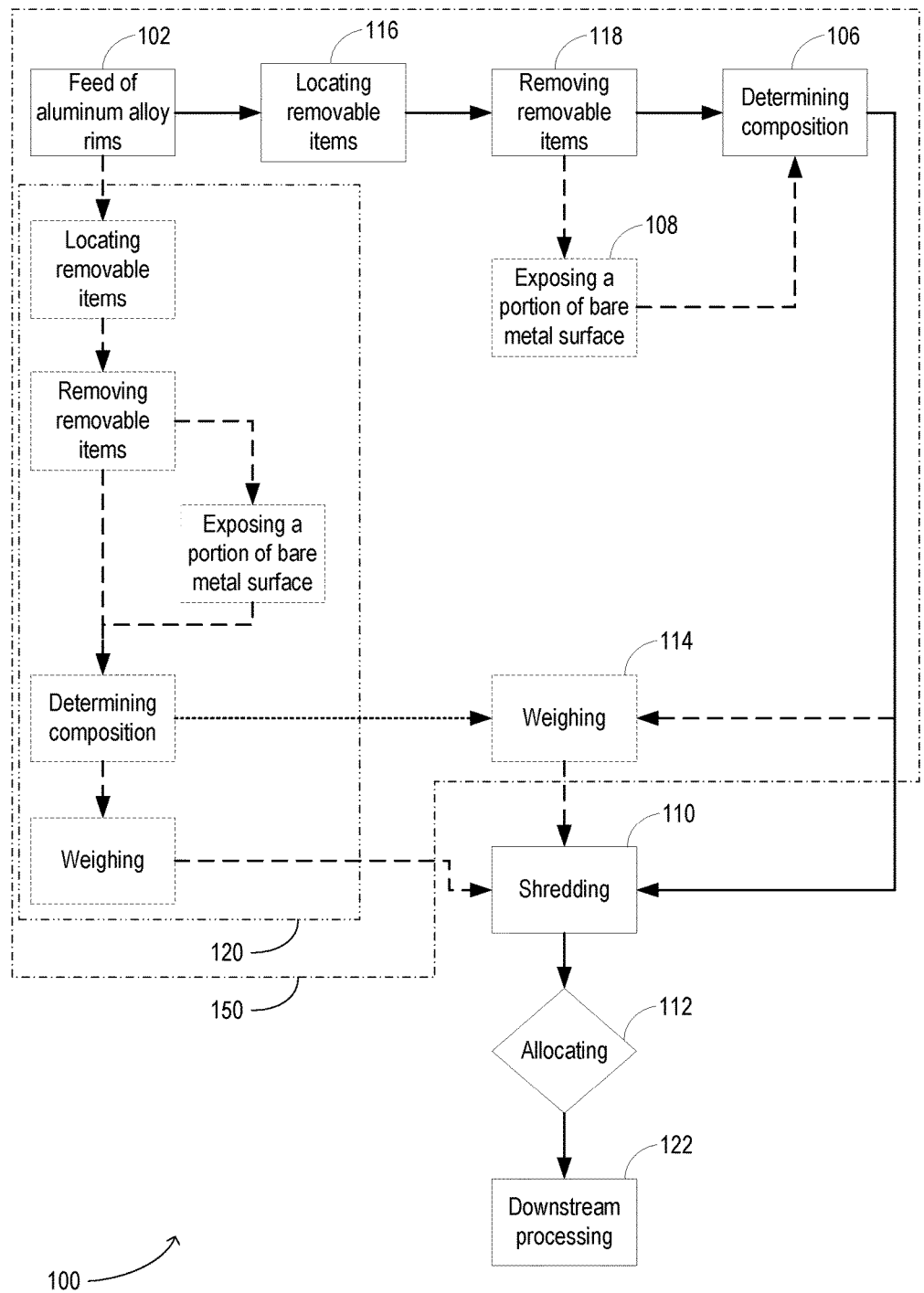
FIG. 1 is a flow diagram illustrating one implementation of a method of recycling aluminum alloy rims.

FIG. 1 illustrates one implementation of a method 100 of recycling aluminum alloy rims. The illustrated method may start with providing a feed 102 of a plurality of aluminum alloy rims of different alloys. The rims may be vehicle rims made from any aluminum alloy currently or in the future used in the manufacture of rims for vehicles. The vehicles may be, for example, cars, trucks or motorcycles. It may be desirable to divide the feed 102 of aluminum alloy rims into one or more batches of recycled aluminum alloy, each batch having an average aluminum alloy composition falling within a particular range of compositions. Accordingly, the method 100 may include determining a plurality of recycled aluminum alloy composition ranges that may be required at a certain point in time. For example, the method 100 may be used to produce three batches of recycled aluminum. A recycled aluminum alloy composition range may be determined for each batch.

In one example, one of the batches may be designated as a rejection batch for rims having an aluminum alloy composition falling outside of the composition ranges determined for the other batches or for rims that are otherwise deemed to be unsuitable for recycling (see, for example, the discussion below relating to removing removable items from the rims). In another example, the rejection batch may be designated for rims having an aluminum alloy composition that would take the average composition of each of the other batches outside the desired composition ranges for those batches if the rims were added to those batches. Rims assigned or allocated 112 to a rejection batch may be stored (for example, see the optional storing step 314a in the implementation of the method 300 illustrated in FIG. 3) and recycled at a later time and may be recycled separately from the other batches of recycled aluminum, or may simply not be processed.

Each desired composition range may include limits for a plurality of constituents. Some limits may include a maximum limit and a minimum limit. Other limits may include maximum limits only. For example, if a batch of recycled aluminum is assembled to make A356.2 aluminum alloy rims, then the composition range for that batch may include limits within which certain constituents of that batch, for example silicon and copper, have to fit in order for the aluminum alloy of the rims made from that batch to qualify as A356.2 aluminum alloy. The limits may be expressed in terms of minimum and maximum weight percent of total alloy weight. There may also be limits on other constituents, such as antimony, which are maximum limits. For example, it may be acceptable or advantageous for a batch of recycled aluminum to contain zero or a negligible weight percent of antimony and unacceptable for the batch to contain more than a specified maximum weight percent of antimony. For each batch and composition range associated with that batch, the limits may differ and may be dictated or chosen based on the purpose(s) for which that batch may be desired.

Determining and satisfying the composition ranges for each batch is a separate issue from removing from each rim removable items such as steel bushings, lead balance weights, extra bolts, studs, coatings (for example, clearcoat or paint), plating materials (for example, chrome plating or material used to anodize a rim), and valve stems. Such removable items may contain constituents for which there may be low limits in the desired composition ranges for each batch or constituents which may otherwise lower the quality of a batch of recycled aluminum. To avoid taking the average composition of an aluminum alloy batch outside of a desired composition range for that batch and to avoid otherwise lowering the quality of that batch, the removable items must be removed. In some cases, depending on the purpose for which a batch of recycled aluminum may be desired, the desired composition range for that batch may allow for the removal of some but not all removable items, or for the removal of a portion of each of the removable items, depending on the nature of the particular removable items.

Thus, the method 100 may include dividing the feed 102 of aluminum alloy rims into a plurality of batches of aluminum alloy rims, each batch of aluminum alloy rims in the plurality of batches of aluminum alloy rims corresponding to an associated recycled aluminum alloy composition range in the plurality of recycled aluminum composition ranges, such that each rim in the plurality of aluminum alloy rims is assigned or allocated 112 to an associated batch in the plurality of batches of aluminum alloy rims based on the composition of that aluminum alloy rim. That is, the method 100 may include dividing the feed 102 by allocating each of the rims to one of the batches of aluminum alloy rims (or, in some cases, batches of shreds of aluminum alloy rims, for implementations where the rims may be shredded 110 prior to being allocated 112 to one of the batches). In order to do this, the method 100 may include a composition analysis step 106. The composition of each of the aluminum alloy rims may be determined 106 by feeding that aluminum alloy rim to a composition analyzer. In a preferred embodiment, the composition analyzer uses laser spectroscopy to determine in real time the composition of each rim.

In one example, the "Laser-Induced Breakdown Spectroscopy" ("LIBS") composition analyzer manufactured by Laser Distance Spectrometry may be adapted as a composition analyzer suitable for the various implementations of the method 100. The LIBS composition analyzer may include a radiation emitter, such as an Nd:YAG laser, and may focus a ray of the Nd:YAG laser on one or more spots on a surface of each of the rims passing in proximity to it at a manufacturer-specified speed and distance. The laser may shine at a frequency ranging from 1 to 20 hertz, thereby raising the temperature of the rim material at the point(s) of contact between the rim material and the laser to above 30,000 degrees Celsius and generating plasma. The plasma may quickly cool down, returning the energized ions into a low energy state. While returning to the low energy state, the ions may emit characteristic radiation. The LIBS composition analyzer may contain one or more sensors that detect the characteristic radiation. A processor may then analyze readings obtained from the sensors and determine 106 from them the concentration of the constituents contained in the material undergoing the temperature change. The processor may be disposed within the composition analyzer. Alternatively, the processor may be a remote processor.

The LIBS composition analyzer manufactured by Laser Distance Spectrometry is designed for metallurgy, mining, coal and phosphate industries. It is designed to provide analysis results that do not depend on the quality of the surface of the analyzed material. Other suitable composition analyzers may also have the capability of performing composition analysis irrespective of surface quality of the material to be analyzed. However, this feature may be undesirable in the context of recycling aluminum alloy rims. Some or all of the rims may be anodized with an anodizing material or have one or more coating or plating—for example, paint, clearcoat, or chrome. The Nd:YAG laser may heat or burn such materials and this may contaminate the laser spectroscopy readings, potentially introducing errors into the composition readings. Heating or burning such coatings or platings may also produce emissions at least some of which may be toxic or detrimental to the environment. Depending on the quantities of emissions produced if the composition analyzer is to be used as intended by the manufacturer, environmental equipment, such as bag houses or specialized filters, as well as environmental permits, may be required. Complying with the resulting environmental, safety and legal requirements may increase the cost of recycling and in some cases may render the recycling commercially unfeasible.

In order to mitigate such complications and potentially reduce emissions, the recycling method 100 may comprise exposing 108 a portion of a bare metal surface of each aluminum alloy rim before determining 106 the composition of that aluminum alloy rim at the portion of the bare metal surface. The steps of exposing the bare metal surface and analyzing the composition of the material at the exposed bare metal surface may be implemented in a number of ways, using any known suitable technology. Once the bare metal surface is exposed, the composition of the exposed material may be determined at the exposed bare metal surface by using a suitable composition analyzer, such as the LIBS composition analyzer described above.

Other suitable composition analyzers may include composition analyzers that use laser spectroscopy or other system that relies on another method of inducing characteristic radiation to be emitted by a material of each rim at a surface of that rim and detecting and analyzing that characteristic radiation to determine a composition 106 of that material. The composition analyzers may detect the characteristic radiation by using any suitable sensor—for example, suitable sensors may include complementary metal-oxide-semiconductor (CMOS), high density, short channel metal-oxide-semiconductor (HMOS), charge-coupled device (CCD), and other types of sensors. For the purposes of the implementations of the recycling method 100, it may be sufficient to assume that the composition of each rim throughout the rim is equal to the composition of the rim material at the one or more spots tested by the composition analyzer.

Suitable composition analyzers may use, for example, radiation emitters such as plasma, electron beam, or any other radiation emitters suitable to heat a material of each rim in at least one spot on a surface of that rim to a point where the material will emit a sufficient quantity and quality of characteristic radiation while cooling down so as to permit a sensor to detect that characteristic radiation and to allow for a processor to determine a composition 106 of the material from that characteristic radiation. The composition analyzer(s) can be adapted to withstand continuous use, as well as typical conditions that may be present in a particular aluminum alloy rim recycling operation. Such conditions may include vibrations resulting from the operation of aluminum alloy rim transfer mechanisms, and dust and other particles produced in the recycling process. Exposing a portion of a bare metal surface of each rim and determining the composition of the rim material at that portion may produce fewer emissions. In a preferred embodiment, the operational speed of a suitable composition analyzer may match or exceed the speed(s) at which aluminum alloy rims may be fed to the composition analyzer.

The rims may be transported to a composition analyzer using a suitable aluminum alloy rim transfer mechanism. The position of a particular rim the bare metal surface of which was exposed may be kept constant relative to the transfer mechanism as the rim is transported to the composition analyzer. The bare metal spot may be exposed at a location of the rim that can be subsequently aligned with, for example, the laser of the composition analyzer without repositioning the rim relative to the transfer mechanism. For example, where the transfer mechanism is a belt conveyor, the position of a rim may be kept constant relative to the conveyor belt.

In another example, a vision system in electronic communication with a servo positioning system may be used. The vision system may track the position of each rim and the location of the exposed portion of the bare metal surface of each rim by analyzing a top surface of each rim and measuring the coordinates of the exposed portion of the bare metal surface relative to a pre-determined reference point. The vision system may communicate the coordinates to the servo positioning system once the rim is transported to the composition analyzer and the servo positioning system may position the rim so as to present the exposed portion of the bare metal surface to the composition analyzer. The servo positioning system may include any combination of known servo-motors and controller(s) suitable for the geometry, size, and weight of the rims to be recycled. Suitable manufacturers of servo positioning systems may include: AB, Yaskawa, and Mitsubishi.

Similar transfer mechanisms may be employed to transport the rims from the composition analyzer station to other stations in the recycling process, and between the other stations that may be part of the recycling process. The position of each rim or of the exposed portion of the bare metal surface may or may not need to be tracked while the rim is transported after the composition analysis step. For example, there may no longer be a need to track the position of the exposed portion of the bare metal surface of a rim after the rim passes the composition analysis step. On the other hand, the position of the rim may need to be tracked when transporting the rim to and between the other stations that may be part of the recycling process. For example, tracking rim position may be required in order to stage parallel upstream processing lines 120, 150 in order to optimize the performance of a shredder into which the lines may converge. Parallel upstream processing 120, 150, shredding, and optimization will be described below.

As mentioned above, determining the composition 106 of each rim at the exposed portion of the bare metal surface may reduce the emissions that may otherwise be produced at the composition analysis step 106. Another benefit of this step may be that the composition of each of the rims may be determined 106 more accurately and in some cases false determinations may be avoided. False determinations may lead to aluminum alloy rims that are suitable for higher value batches being allocated 112 to lower value batches, or perhaps even being allocated 112 to a rejection batch.

In the example of a LIBS composition analyzer, an inaccurate composition reading or a false determination may occur where, for a particular rim, depending on the thickness and the type of coating or plating material that may be present on the rim, the Nd:YAG laser may not penetrate or may insufficiently penetrate the coating or plating material. In some cases, a false determination of the material of which a particular rim may be made may result in that rim being added to a wrong batch, thereby causing the average composition of that batch to fall outside of the desired range of compositions for that batch.

By removing any coating or plating, or a substantial portion of the coating or plating, at the spot(s) to be tested by the composition analyzer, the likelihood of the occurrence of false determinations may be reduced and the accuracy of at least some of the composition readings may be improved. In some embodiments, the composition analyzer may be capable of removing the required amount of coating or plating using its radiation emitter; however, for the reasons stated above, using, for example a laser, for this purpose may not be desirable. In a preferred embodiment, the bare metal surface may be exposed by using one or more suitable mechanical devices.

For example, suitable mechanical devices may include one or more of: a drill, a burr, or an end mill. In a system, the step of exposing 108 a portion of a bare metal surface of each aluminum alloy rim may be implemented as a manual or as an automated step, or as a combination of manual and automated steps. Any suitable combination of known technology and controllers may be used to implement this step in an automated manner. For example, the rims may be transported to a station where the rims pass by an automatic cutting tool, such as an end mill, which removes an amount of surface material from a spot on each of the rims so as to create an exposed bare metal surface on each of the rims.

In some cases, it may be desirable for the method 100 to further comprise, for at least one rim in the plurality of aluminum alloy rims, or for each rim in the plurality of aluminum alloy rims, determining a weight (i.e. weighing) 114 of that aluminum alloy rim. In these cases, dividing the feed of aluminum alloy rims into the plurality of batches of aluminum alloy rims may comprise, for that aluminum alloy rim, allocating 112 that aluminum alloy rim to the associated batch in the plurality of batches of aluminum alloy rims based on both the composition of that aluminum alloy rim and the weight of that aluminum alloy rim. These steps may allow, for each batch of aluminum alloy rims in the plurality of aluminum alloy rims, determining, updating and storing batch-specific variables.

For each batch, the batch-specific variables may comprise a batch-specific total weight of aluminum alloy rims previously allocated 112 to that batch, and a batch-specific average composition of aluminum alloy rims previously allocated 112 to that batch. The batch-specific average composition of aluminum alloy rims previously allocated 112 to that batch may be calculated based on the weight and the composition of each aluminum alloy rim previously allocated 112 to that batch. In some embodiments, for example as shown 320 in the implementation of the method 300 in FIG. 3, weighing 114 each aluminum alloy rim may be contemporaneous, or slightly before or after determining 106 a composition of that rim 106. Each rim may be individually weighed 114.

In some example implementations of method 100, for each aluminum alloy rim, allocating 112 that aluminum alloy rim to the associated batch in the plurality of batches of aluminum alloy rims can be based on, in addition to the composition of that aluminum alloy rim and the weight of that aluminum alloy rim, the batch-specific total weight of aluminum alloy rims previously allocated 112 to that batch and the batch-specific average composition of aluminum alloy rims previously allocated 112 to that batch. These steps may allow for more accurately calculating, keeping track of, and controlling the batch-specific average composition and the batch-specific total weight of each of the batches of recycled aluminum. These steps may also increase the efficiency of the recycling method 100. The feed 102 of aluminum alloy rims may include rims having a composition that falls outside each of the recycled aluminum alloy composition ranges.

The comparison of the weight and composition of each rim with the batch-specific total weight and the batch-specific average composition of each batch and the required composition range for each of the batches may show that a particular rim would not take the average composition of at least one of the batches outside of the required composition range of that batch. It this case, that rim may be allocated 112 to one of the at least one of these batches. The comparison may also show that that the rim would take the average composition of any one of the batches outside of the required composition range of that batch, or unacceptably close to the boundary of the composition range. In that case, the rim may be allocated 112 to a rejection batch. A system, for example the system 200 illustrated in FIG. 2, may allocate 112 the rims automatically. Non-aluminum or otherwise unsuitable rims may be allocated to a rejection batch automatically or manually, depending on the particular recycling operation.

One or more of the aluminum alloy rims in the feed 102 may have one or more removable items. The removable items may include any one or more of steel bushings, lead balance weights, extra bolts, studs, coatings (for example, clearcoat or paint), plating materials (for example, chrome plating or material used to anodize a rim), and valve stems. The presence of the removable items in the recycling process may be undesirable in that it may reduce the purity of a resulting recycled aluminum alloy batch and in some cases may take the average composition of that batch outside of the recycled aluminum alloy composition range required for that batch. Also, as described below, one or more shredders may be used in the recycling process. Depending on the type of shredder(s) used, some types of removable items, such as steel bushings or other steel items, may damage the shredder(s). Accordingly, depending on the particular removable items present on a particular rim, it may be desirable to remove 118 some, portions of, or all of the removable items. Depending on the type of shredder(s) and if such items, or portions of such items, cannot be removed from a particular rim, it may be necessary to reject that rim from the recycling process.

Thus, the method 100 may include locating 116 and removing 118 removable items steps. One or both of these steps may be performed manually or automatically, or in a combination of manual and automatic steps, depending on the particular recycling operation. The rim may be rejected by manually taking it out of the feed of aluminum alloy rims 102 or by allocating 112 it to a rejection batch. The rim may also be rejected manually after visual inspection of the rim after the removal of removable items step 118, or automatically after automated verification of whether the removable items that were located were removed. In order to automate at least one of these steps, the rims may be fed to a measurement system which may determine the number, if any, of the removable items on each of the rims 116. The measurement system may also determine the coordinates 116 of each of the removable items, relative to, for example, a reference point on the corresponding rim or relative to a reference point on the aluminum alloy rim transfer mechanism by which the corresponding rim may be transported. In a system, this step may be automated using any suitable combination of known technology and controllers. For example, a laser measurement system in combination with an indexing conveyor, a walking beam transfer, a robot, or a pick-and-place unit can be used.

Accordingly, method 100 for recycling aluminum alloy rims illustrated in FIG. 1 in accordance with an aspect of an embodiment of the present invention, comprises providing a feed 102 of aluminum alloy rims and locating 116 the removable items, if any, on each of the rims in the feed 102. As shown, the locating step 116 may include determining the number of and the coordinates of the removable items, if any, on each of the rims and may be implemented using a suitable measurement system. As shown, locating 116 removable items may be followed by removing 118 at least some of or at least portions of the removable items from each of the rims. In a particular example, removal 118 of removable items includes an automated bushings press-out. Bushings press-out may be achieved by any suitable system. The suitable system may include one or more of a combination of, for example, a multi-axes servo driven press operating automatically based on the coordinates of the bushings determined at the measurement step 116, a dedicated press having interchangeable sets of press-out tools for particular types of bushings, and a rotary table in combination with single axis press.

After the removal of removable items 118, each of the rims may be visually inspected to confirm that the removable items have been removed 118. An inspector may then decide, for each rim, whether to take the rim out of the recycling process, or to direct the rim for further processing. Alternatively, the visual inspection step may be automated by, for example, recirculating each of the rims to the measurement system. In this case, for each rim, once the measurement system locates 116 any remaining removable items on that rim, a processor may compare the remaining removable items data to the data for that rim obtained before the removal of removable items 118 and may generate a control signal to either direct the rim for further processing or to allocate 112 the rim to a rejection batch. Where a rim is directed for further processing, the method 100 may proceed to a step of determining a composition 106 of that rim. Preferably, the method 100 includes exposing a portion of a bare metal surface 108 of each rim prior to determining the composition 106 of that rim at that portion of the bare metal surface.

The method 100 may further include shredding 110 the rims in the feed 102 of aluminum alloy rims. In some implementations of the method 100, the rims may be shredded 110 before being allocated 112 to one of the batches. In other implementations of the method 100, the rims may be shredded 110 after being allocated 112 to one of the batches and may or may not be shredded if allocated 112 to a rejection batch, depending on the requirements of the particular recycling operation and the configuration of the system performing the method 100. In a preferred implementation of the method 100, the shredding step 110 is performed downstream from the determining composition 106 and the weighing 114 steps, as it is simpler, in many cases, to determine the composition of an intact rim, as opposed to the shredded pieces of a rim. In the implementation shown in FIG. 1, the shredding step 110 takes place after the weighing step 114. In these embodiments, there may be no need to continue distinguishing the shreds of one rim from the shreds of another rim provided they have all been allocated 112 to the same batch.

Any suitable shredder known in the art may be used. For example, aluminum alloy car rims may be supplied to a hopper of a conventional shredding apparatus, such as the SSI Series 45H shredder available from SSI Shredding Systems Inc. at 9760 SW Freeman Drive, Wilsonville, Oreg., 97070-9286, USA. This shredding apparatus may include a cutter box housing the cutters, which can be mounted on parallel shafts that rotate horizontally in opposite directions. The feed hopper can be located above the cutter box. Due to the force of gravity, the rims placed in the feed hopper can then be fed downwardly into the proper location where they can be engaged by the cutters and torn or cut into shreds. Preferably, the rims are cut or torn into shreds of two to three inches in length and, more preferably, approximately two inches in length.

In a preferred implementation of the method 100, the shredder is switchable between serving the different batches or paths of travel that may be provided for one or more of the batches. For example, the shredder may be first selected to shred the rims allocated 112 to one of the batches, and may subsequently be switched to shredding 110 the rims allocated 112 to another one of the batches, depending on the availability of rims in the feed 102 and the demand(s) for different compositions of recycled aluminum that may exist at the time. When the rims are shredded 110, at least portions of the removable items such as valve stems may be freed up such that a percentage of these may be removed from the recycling process by a magnetic separator and, optionally, an eddy current separator.

The shredding 110 may also produce fines and dirt. Preferably, these byproducts may be separated from the shreds by method steps such as screening. For example, the shreds may be fed to a vibrating screen. The fines and dirt may pass through the vibrating screen and may be preferably recovered by melting or an alternative process. The shredded pieces may need to be further cleaned, for example, by shot blasting. The steps of screening, recovery of fines and dirt, magnetic and eddy current separation, and shot blasting are known in the art may be implemented as described in the prior art. For example, these steps and the apparatuses corresponding to these steps may be implemented as described in U.S. Pat. No. 6,983,901. These steps may be referred to collectively as downstream processing. The steps that may be performed prior to the shredding step 110 may be referred to as upstream processing. It will be appreciated that a step may in one implementation of the method 100 be part of upstream processing and may be part of downstream processing in another implementation of the method 100.

In some embodiments, depending on the kind and capacity of the shredder(s) being used, shredding 110 may be able to occur at a much higher rate than the upstream processing steps 150 of locating removable items 116, removing removable items 118, determining 106 a composition of the rim (including exposing up portion of bare metal surface 108 according to some embodiments) and weighing the rim 114. In these embodiments, multiple lines may be provided upstream of shredding 110 for parallel upstream processing 120 to sort rims into different batches. The upstream processing lines may be staged to not interfere with each other and the shredder can then be switched between shredding for the different batches. By using parallel upstream processing 120, the combined upstream processing rate can be increased to match, or at least be closer to, the processing rate of the shredder.

Figure 2:
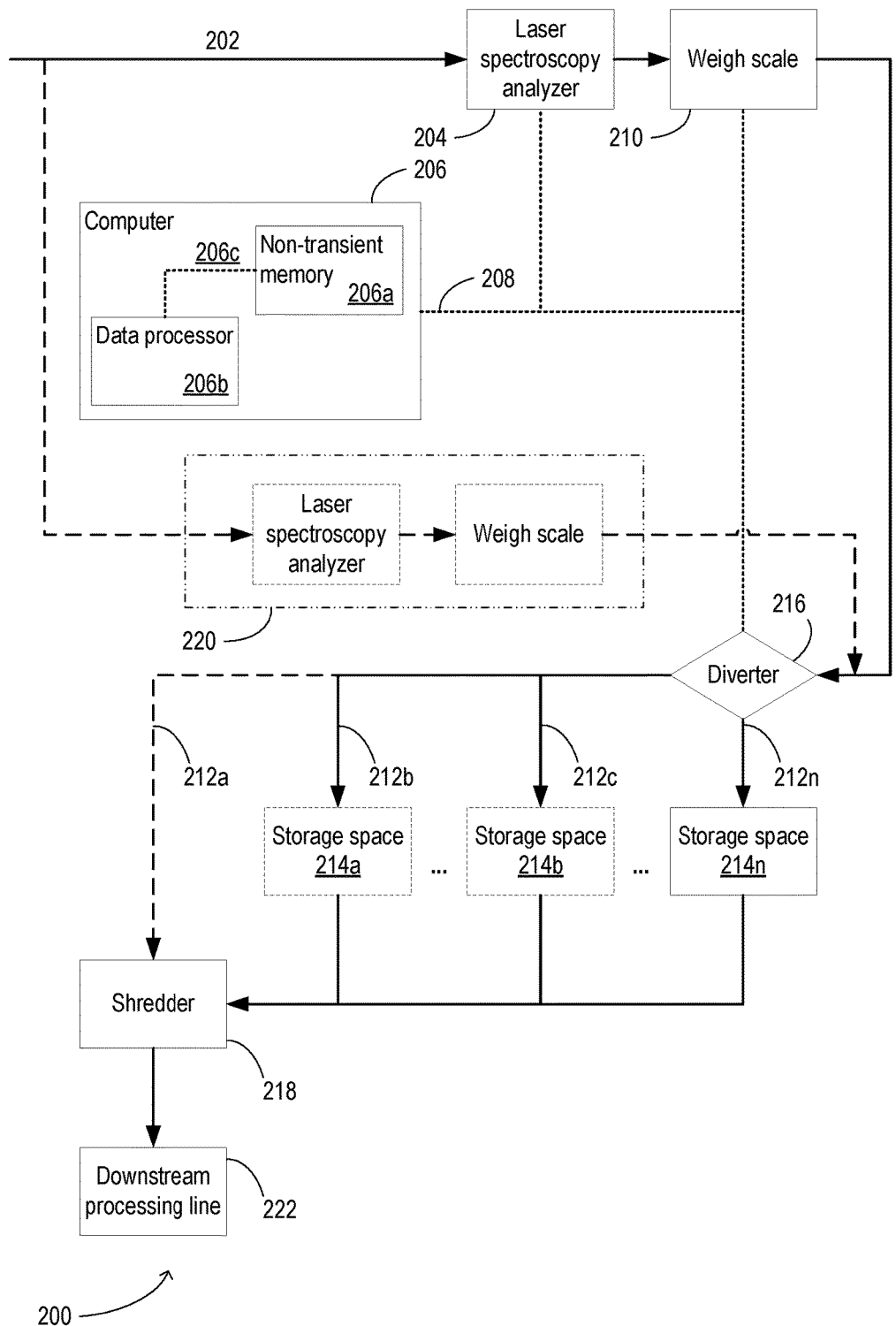
FIG. 2 is a schematic illustrating a system for recycling aluminum alloy rims, according to one embodiment.

FIG. 2 illustrates an embodiment of a system 200 for recycling aluminum alloy rims. The system 200 comprises an aluminum alloy rim conveyor 202 for providing a feed of a plurality of aluminum alloy rims of different alloys and a composition analyzer that is a laser spectroscopy analyzer 204 for analyzing and thereby determining the composition of each rim in the plurality of aluminum alloy rims. The laser spectroscopy analyzer 204 is operable to determine 106 a composition of each rim in the plurality of aluminum alloy rims and is positioned to receive each rim in the plurality of aluminum alloy rims from the aluminum alloy rim conveyor 202. The system 200 further comprises a computer 206 in electronic communication 208 with the laser spectroscopy analyzer 204 to receive, for each rim in the plurality of aluminum alloy rims, the composition of that rim. The computer 206 comprises a non-transient memory 206*a* and a processor 206*b* in electronic communication 206*c* with the non-transient memory 206*a*. The non-transient memory 206*a* has stored thereon a plurality of recycled aluminum alloy composition ranges. The processor 206*b* is operable to allocate 112 each of the rims to a batch in a plurality of batches of aluminum alloy rims based on the composition of that rim.

As shown, a weigh scale 210 may be disposed downstream of the laser spectroscopy analyzer 204 and may receive each of the rims from the conveyor 202. The weigh scale 210 may be in electronic communication 208 with the computer 206. The weigh scale 210 may be operable to determine a weight 114 of each rim in the plurality of aluminum alloy rims. The processor 206*b* may be operable to allocate 112 each rim to a batch in the plurality of batches of aluminum alloy rims based on both the weight and the composition of that rim. For each batch in the plurality of batches of aluminum alloy rims, the system 200 may store in the non-transient memory 206*a* of the computer 206 a plurality of batch-specific variables. The batch-specific variables may comprise a batch-specific total weight of aluminum alloy rims previously allocated 112 to that batch, and a batch-specific average composition of aluminum alloy rims previously allocated 112 to that batch.

The batch-specific total weight of aluminum alloy rims previously allocated 112 to that batch may be calculated based on the sum of the weights of each aluminum alloy rim previously allocated 112 to that batch. The batch-specific average composition of aluminum alloy rims previously allocated 112 to that batch may be calculated based on the weight and the composition of each aluminum alloy rim previously allocated 112 to that batch. For each aluminum alloy rim, the system 200 may allocate 112 that aluminum alloy rim to the associated batch in the plurality of batches of aluminum alloy rims based on, in addition to the composition of that aluminum alloy rim and the weight of that aluminum alloy rim, the batch-specific total weight of aluminum alloy rims previously allocated 112 to that batch and the batch-specific average composition of aluminum alloy rims previously allocated 112 to that batch.

As shown, the system 200 further comprises a diverter 216 and a plurality of paths of travel 212*a*, 212*b*, 212*c*, . . . , 212*n* for the feed of the plurality of aluminum alloy rims downstream from the laser spectroscopy analyzer 204, and a plurality of storage spaces 214*a*, 214*b*, . . . , 214*n* downstream of the diverter 216. The system 200 may allocate 112 each of the rims to one of the batches by diverting and transporting each rim in the plurality of aluminum alloy rims along a path of travel 212*a*-212*n* selected out of the plurality of the paths of travel 212*a*-212*n*. In other words, the system 200 may transport each rim in the plurality of aluminum alloy rims along a selected path of travel 212*a*-212*n* in the plurality of paths of travel 212*a*-212*n* based on the batch in the plurality of batches of aluminum alloy rims selected by the processor 206*b* for that rim. This logic may be implemented, for example, as follows. The laser spectroscopy analyzer 204 may determine the composition 106 of each of the rims in the feed 102 and may, for each of the rims, transmit the reading for that rim to the computer 206.

The computer 206 may compare the reading and the weight of the rim to the aluminum alloy composition ranges and the batch-specific total weight and the batch-specific average composition of each batch, may calculate whether the rim may be allocated 112 to one or more than one of the batches without taking the average composition of that batch (or batches) outside of the composition range desired for that batch (or batches), and may produce a control signal reflecting the result of this calculation. The computer 206 may then allocate 112 the rim by sending the control signal to the diverter 216. In implementations of the method that do not involve batch-specific variables, the computer 206 may simply compare the composition reading of each rim with the required aluminum alloy composition range of each of the batches. If the reading is outside of each of the ranges, the computer 206 may produce and send a signal to the diverter 216 to allocate 112 the rim to a rejection batch, if one is designated. Depending on the particular recycling operation, the system 200 may include more than one diverter 216.

Alternatively, the computer 206 may also divert the rim out of the recycling process, even if the allocation 112 of that rim to one of the batches would not take the average composition of that batch outside of the aluminum alloy composition range required for that batch. For example, a rim that is exceptionally pure may be diverted out of the recycling process so that the computer 206 or an operator can subsequently make a decision about where to allocate 112 that rim. Alternatively, a rim that could be allocated 112 to one of the batches without taking the average composition of that batch outside of the aluminum alloy composition range required for that batch, but which would bring the average composition of that batch unacceptably close to the boundary of the aluminum alloy composition range required for that batch, might be diverted out of the recycling process, so that a decision of whether or not to allocate 112 that rim could be delayed until more information is available, as the batch is closer to completion, about whether that rim can be safely allocated 112 to that batch.

Where an aluminum alloy rim is of exceptional purity such that it can be allocated 112 to more than one of the batches, it may be, in some cases, advantageous to allocate 112 that aluminum alloy rim to the highest value alloy batch. In other cases, it may be more advantageous to allocate 112 that aluminum alloy rim to a particular batch having a batch-specific average composition that is close to a boundary of the composition range required for that batch. In this way, that batch can be made more pure, such that potentially allocating 112 a few exceptionally pure rims to that batch can preserve or increase the value of that entire batch.

As shown in FIG. 2, each storage space 214a-214n in the plurality of storage spaces 214a-214n may be part of a different path of travel 212a-212n in the plurality of paths of travel 212a-212n. As shown by the path of travel 212a, one or more of the paths of travel 212a-212n may have no storage space associated with the one or more paths of travel 212a-212n. Each of the paths of travel 212a-212n may include a conveyor operable independently of the conveyors associated with the other paths of travel 212a-212n. A shredder 218 may be disposed downstream of the diverter 216 and the paths of travel 212a-212n may converge into the shredder 218. Downstream processing stations 220 may be disposed downstream of the shredder 218 and may include shot blasting, magnetic and eddy current separation steps. As noted above, these steps may be implemented for example as described in U.S. Pat. No. 6,983,901.

Depending on the particular recycling operation, the system 200 may include multiple shredders 218. A shredder 218 may be one of the more expensive components of the recycling system 200. Accordingly, it may be desirable to minimize the quantity of shredders 218 used in the recycling process while maximizing the output of the recycling process. As shown in FIG. 2, the system 200 includes one shredder 218. The speed at which the shredder 218 may shred each rim may exceed the speed of upstream processing. In such cases, the recycling method may include one or more parallel upstream processing lines 220. For example, where the shredder 218 may shred 110 each of the rims twice as quickly as each of the rims may be processed upstream 150, the provision of two upstream processing lines 220 in parallel may allow to utilize the shredder 218 at or close to its shredding capacity and thus maximize the utility of the shredder 218 and the output of the recycling process.

In cases where the system 200 is implemented with parallel upstream processing 220, the computer 206 may be programmed to stage the upstream processing 220 in order to ensure that the outputs from the upstream processing lines 220 do not interfere with each other and to ensure that each of the rims may be individually allocated 112 to one of the batches so as to avoid incorrect allocations. In these implementations, as mentioned above, the position of each of the rims may be tracked to facilitate the staging. It will be appreciated that this staging may be implemented using any suitable program code and hardware by a person skilled in the art without the use of inventive ingenuity but based on the logic described in this document.

Particular requirements of the staging, such as particular shredding speeds, delays, sensing steps monitoring when one stage or a combination of stages of the method 100 are completed, may be dictated by the particular combination of components used in the system 200, and by their operating characteristics (such as speed). In some cases, the system 200 may be further optimized by minimizing the number of components carrying out the recycling method 100. For example, depending on the characteristics of the particular components used in the system 200, it may be possible to use a single weigh scale 210 between two upstream processing lines 220 without decreasing the overall output of the processing lines 220.

Figure 3:
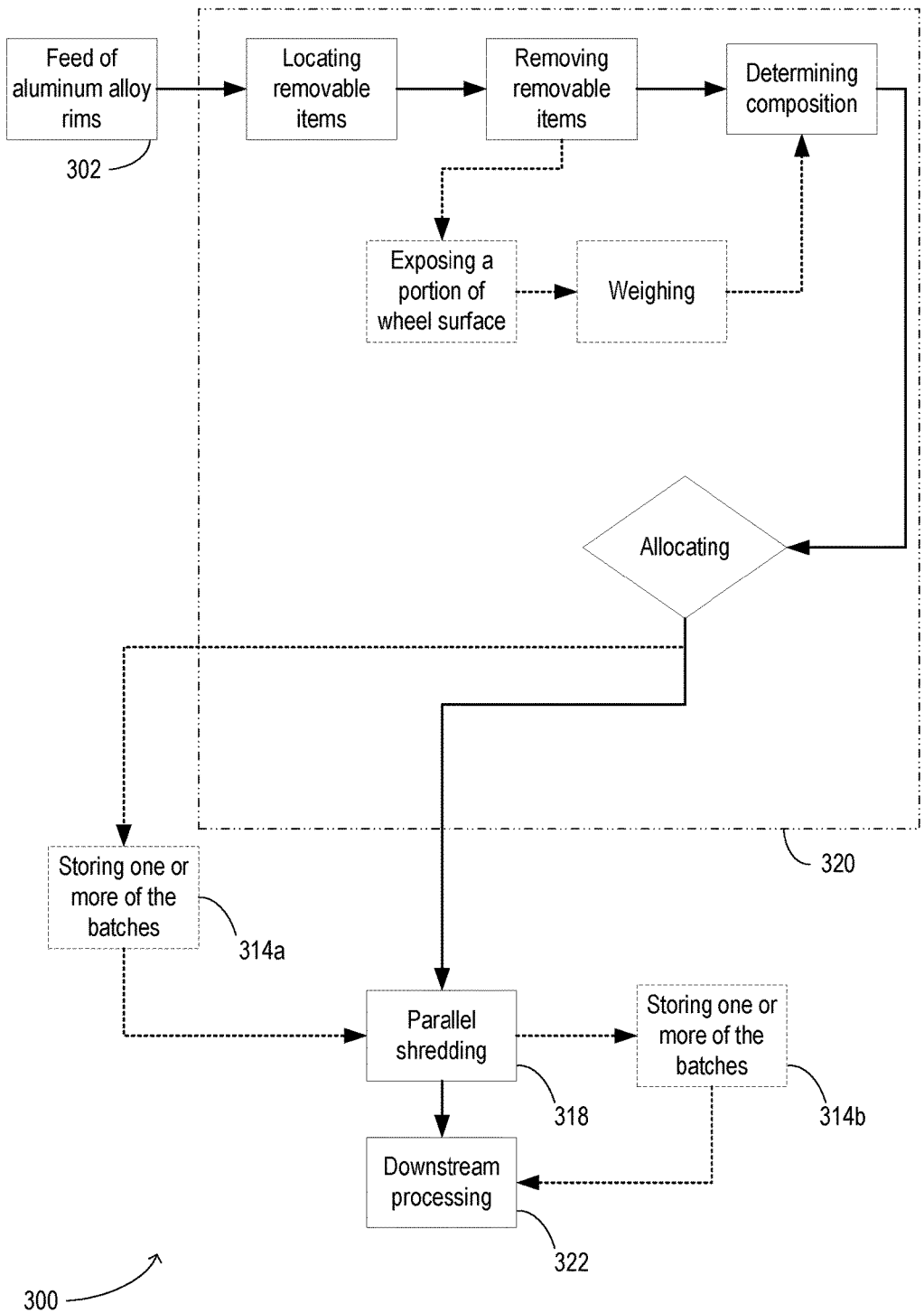
FIG. 3 is a flow diagram illustrating another implementation of the method of recycling aluminum alloy rims.

FIG. 3 illustrates another implementation of the method 300 for recycling aluminum alloy rims. The method 300 may comprise upstream processing 320 and downstream processing 322 steps and variations of implementations of those steps 320, 322 that are analogous to those described in relation to the method 100. Also, cheaper but slower shredders may be or may become available. Thus, depending on the particular aluminum alloy rim recycling operation, it may be or may become advantageous to use a plurality of such shredders. As shown, the method 300 includes shredding 318 the rims in a plurality of parallel shredding steps 318, which may be collectively referred to as a parallel shredding step 318, in which a plurality of shredders may be used, with appropriate staging.

It will be appreciated that depending on the number and the speed of shredders, it may be advantageous or necessary for the method 300 to include storing 314a, 314b the one or more of the batches in one or more storage spaces 214a, 214b, . . . , 214n prior to sending them for shredding 318. Storage requirements and storage times may be dictated by the availability of and the particular compositions of available rims of different aluminum alloys, as well as the demand(s) for recycled aluminum batches having particular compositions that may be occurring at those particular times. Similar considerations may apply to temporarily storing the shreds in one or more of the batches after the shredding step 318. Temporarily storing 314a, 314b one or more of the batches may provide a more optimal operation of the method 300 and may facilitate matching, for any given point in time, the supply of rims in the feed 302 with one or more demands for recycled aluminum occurring at that point in time.

While the above description provides examples of one or more apparatus, methods, or systems, it will be appreciated that other apparatus, methods, or systems may be within the scope of the claims as interpreted by one of skill in the art.

The invention claimed is:

1. A method of recycling aluminum alloy rims, the method comprising:
providing a feed of a plurality of aluminum alloy rims of different alloys;
for each rim in the feed of aluminum alloy rims, determining a composition of that aluminum alloy rim;
determining a plurality of recycled aluminum alloy composition ranges; and
dividing the feed of aluminum alloy rims into a plurality of batches of aluminum alloy rims, each batch of aluminum alloy rims in the plurality of batches of aluminum alloy rims corresponding to an associated recycled aluminum alloy composition range in the plurality of recycled aluminum composition ranges, such that each rim in the plurality of aluminum alloy rims is allocated to an associated batch in the plurality of batches of aluminum alloy rims based on the composition of that aluminum alloy rim,
where determining the composition of each aluminum alloy rim is performed by heating a material of that rim in at least one spot on a surface of the rim to a point where the material will emit a characteristic radiation while cooling down, using a sensor to detect that characteristic radiation, and using a processor to analyze that characteristic radiation to determine the composition of the material.

2. The method of recycling aluminum alloy rims as defined in claim 1, wherein the heating is performed by focusing a ray of a laser on the at least one spot on the surface of that rim.

3. The method of recycling aluminum alloy rims as defined in claim 1, further comprising exposing a portion of a bare metal surface of the aluminum alloy rim before determining the composition of each aluminum alloy rim and wherein the at least one spot on the surface of the rim is located at that portion of the bare metal surface.

4. The method of recycling aluminum alloy rims as defined in claim 1, further comprising, for at least one rim in the plurality of aluminum alloy rims, determining a weight of that aluminum alloy rim, and wherein dividing the feed of aluminum alloy rims into the plurality of batches of aluminum alloy rims comprises, for that aluminum alloy rim, allocating that aluminum alloy rim to the associated batch in the plurality of batches of aluminum alloy rims based on both the composition of that aluminum alloy rim and the weight of that aluminum alloy rim.

5. The method of recycling aluminum alloy rims as defined in claim 1, further comprising for each rim in the plurality of aluminum alloy rims, determining a weight of that aluminum alloy rim, and wherein dividing the feed of aluminum alloy rims into the plurality of batches of aluminum alloy rims comprises, for each aluminum alloy rim, allocating that aluminum alloy rim to the associated batch in the plurality of batches of aluminum alloy rims based on both the composition of that aluminum alloy rim and the weight of that aluminum alloy rim.

6. A method of recycling aluminum alloy rims, the method comprising:
providing a feed of a plurality of aluminum alloy rims of different alloys;
for each rim in the feed of aluminum alloy rims, determining a composition of that aluminum alloy rim;
determining a plurality of recycled aluminum alloy composition ranges;
diving the feed of aluminum alloy rims into a plurality of batches of aluminum alloy rims, each batch of aluminum alloy rims in the plurality of batches of aluminum alloy rims corresponding to an associated recycled aluminum alloy composition range in the plurality of recycled aluminum composition ranges, such that each rim in the plurality of aluminum alloy rims is allocated to an associated batch in the plurality of batches of aluminum alloy rims based on the composition of that aluminum alloy rim;
for at least one rim in the plurality of aluminum alloy rims, determining a weight of that aluminum alloy rim, where diving the feed of aluminum alloy rims into the plurality of batches of aluminum alloy rims comprises, for that aluminum alloy rim, allocating that aluminum alloy rim to the associated batch in the plurality of batches of aluminum alloy rims based on both the composition of that aluminum alloy rim and the weight of that aluminum alloy rim; and,
for each batch of aluminum alloy rims in the plurality of aluminum alloy rims, determining, updating and storing batch-specific variables, wherein
the batch-specific variables comprise a batch-specific total weight of aluminum alloy rims previously allocated to that batch, and a batch-specific average composition of aluminum alloy rims previously allocated to that batch,
the batch-specific average composition of aluminum alloy rims previously allocated to that batch is calculated based on the weight and the composition of each aluminum alloy rim previously allocated to that batch, and
for each aluminum alloy rim, allocating that aluminum alloy rim to the associated batch in the plurality of batches of aluminum alloy rims is based on, in addition to the composition of that aluminum alloy rim and the weight of that aluminum alloy rim, the batch-specific total weight of aluminum alloy rims previously allocated to that batch and the batch-specific average composition of aluminum alloy rims previously allocated to that batch.

7. The method as defined in claim 1, further comprising, for each rim in the plurality of aluminum alloy rims, removing at least a portion of at least one removable item on that rim.

8. The method as defined in claim 7, wherein the at least one removable item includes at least one of: a steel bushing, a lead balance weight, an extra bolt, a stud, a coating, an anodizing material, and a plating material.

9. The method of recycling aluminum alloy rims as defined in claim 6, wherein determining the composition of each aluminum alloy rim is performed by heating a material of that rim in at least one spot on a surface of the rim to a point where the material will emit a characteristic radiation while cooling down, using a sensor to detect that characteristic radiation, and using a processor to analyze that characteristic radiation to determine the composition of the material.

10. The method of recycling aluminum alloy rims as defined in claim 9, wherein the heating is performed by focusing a ray of a laser on the at least one spot on the surface of that rim.

11. The method of recycling aluminum alloy rims as defined in claim 9, further comprising exposing a portion of a bare metal surface of the aluminum alloy rim before determining the composition of each aluminum alloy rim and wherein the at least one spot on the surface of the rim is located at that portion of the bare metal surface.

12. The method of recycling aluminum alloy rims as defined in claim 6, wherein determining the weight of the aluminum alloy rim for at least one rim in the plurality of aluminum alloy rims comprises, for each rim in the plurality of aluminum alloy rims, determining the weight of that aluminum alloy rim, and wherein dividing the feed of aluminum alloy rims into the plurality of batches of aluminum alloy rims comprises, for each aluminum alloy rim, allocating that aluminum alloy rim to the associated batch in the plurality of batches of aluminum alloy rims based on both the composition of that aluminum alloy rim and the weight of that aluminum alloy rim.

13. The method as defined in claim 6, further comprising, for each rim in the plurality of aluminum alloy rims, removing at least a portion of at least one removable item on that rim.

14. The method as defined in claim 13, wherein the at least one removable item includes at least one of: a steel bushing, a lead balance weight, an extra bolt, a stud, a coating, an anodizing material, and a plating material.

* * * * *

UNITED STATES PATENT AND TRADEMARK OFFICE
CERTIFICATE OF CORRECTION

PATENT NO. : 10,220,418 B2
APPLICATION NO. : 15/333361
DATED : March 5, 2019
INVENTOR(S) : Daniel Bitton Page 1 of 1

It is certified that error appears in the above-identified patent and that said Letters Patent is hereby corrected as shown below:

In the Claims

Column 15, Claim 6, Line 54: delete the word "diving" and replace with --dividing--.

Signed and Sealed this
Seventh Day of May, 2019

Andrei Iancu
*Director of the United States Patent and Trademark Office*